United States Patent [19]

Hiltebrandt

[11] 4,027,510
[45] June 7, 1977

[54] FORCEPS

[76] Inventor: Siegfried Hiltebrandt, August-Lammle-Strasse 16, 7134 Knittlingen, Germany

[22] Filed: May 15, 1974

[21] Appl. No.: 470,176

[52] U.S. Cl. .................................. 72/37; 72/410; 128/6

[51] Int. Cl.² .................... A61B 1/06; A61B 17/42

[58] Field of Search ............... 72/37, 410; 128/4–8, 128/325, 326, 334, 346, 303 A; 227/19

[56] References Cited

UNITED STATES PATENTS

| 1,624,716 | 4/1927 | Cerbo | 128/7 |
| 2,162,681 | 6/1939 | Ryan | 128/6 |
| 2,691,370 | 10/1954 | Wallace | 128/6 |
| 3,032,039 | 5/1962 | Beaty | 128/326 |
| 3,774,438 | 11/1973 | Weston | 72/410 |
| 3,777,538 | 12/1973 | Weatherly et al. | 72/410 |
| 3,856,016 | 12/1974 | Davis | 128/325 |

Primary Examiner—E. M. Combs

[57] ABSTRACT

This invention relates to forceps instruments, particularly those used for fitting tantalum clips for sealing off the Fallopian tubes in the human female. Such instruments ordinarily comprise a barrel with a handle at the proximal end thereof to open and close jaws of the forceps for the clips at the distal end of the barrel, the surgeon observing the operational area by means of an optical system that includes a viewing tube associated with the forceps instrument. In accordance with the invention, the viewing tube extends centrally through the barrel which is longitudinally movable to open and close the forceps jaws; the viewing tube terminates in a straight line so as to give the surgeon uninterrupted vision between the forceps jaws.

1 Claim, 4 Drawing Figures

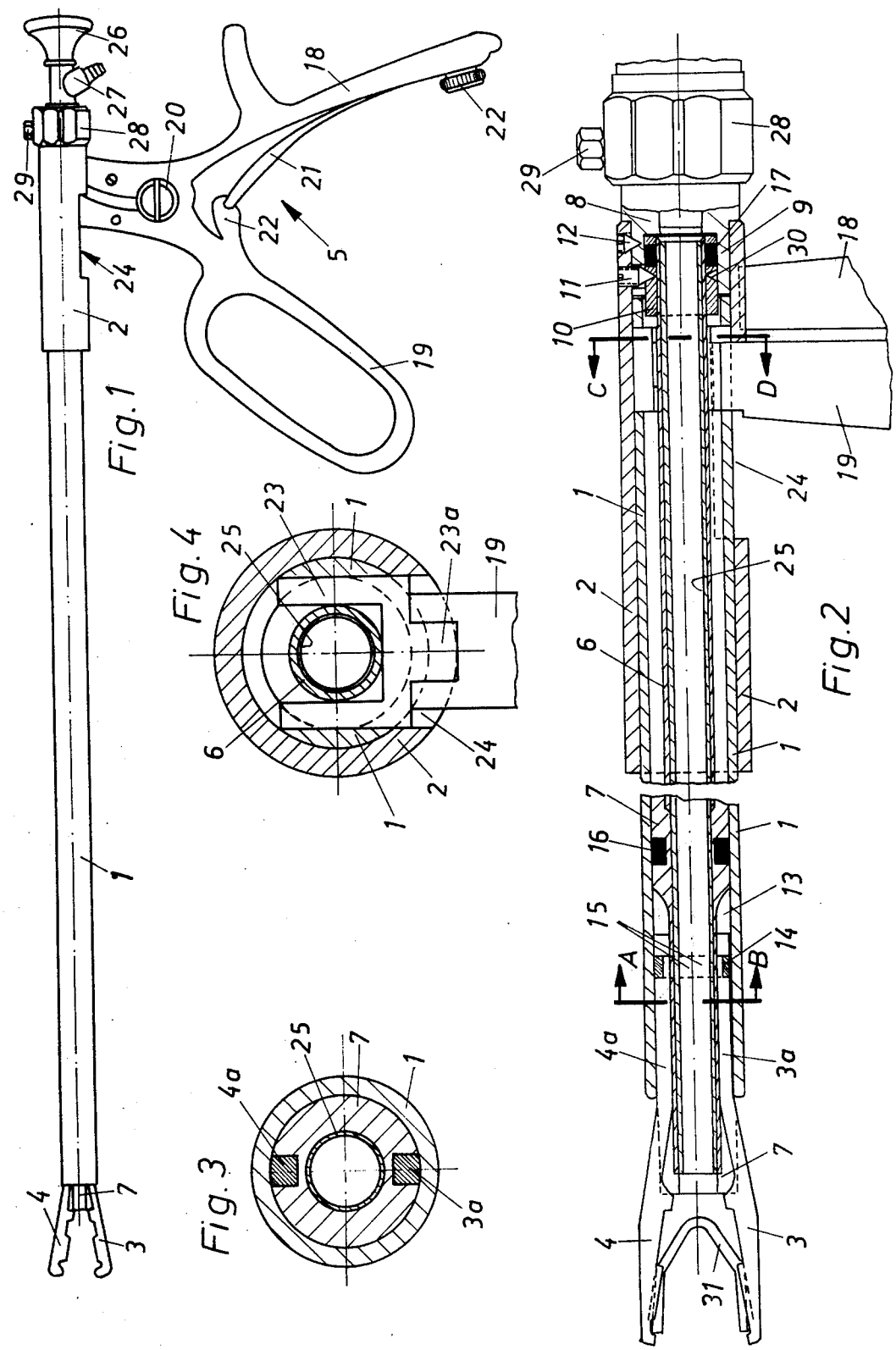

FORCEPS

BACKGROUND OF THE INVENTION

The present invention relates to forceps instruments for fitting tantalum clips for sealing off the fallopian tubes in the human female, the instrument consisting of a barrel with a handle at the prosimal end to close and open forceps for the clips at the distal end while observation takes place by means of an optical system.

In so-call gynaecological laparoscopy, to seal off the Fallopian tubes for contraceptive purposes clips made of tantalum are fitted using a special forceps instrument while observation takes place visually. Two forceps units are used for this, namely the forceps proper for fitting the clips (hereinafter referred to as the clip forceps), and a smaller pair of forceps or a movable hook (hereinafter referred to as the tube forceps) to allow the Fallopian tube to be brought within the reach of the actual clip forceps and to allow it to be taken hold of more satisfactorily. In such known devices the optical system is housed in a special tube near the clip forceps. This is a disadvantage both because the immediate area of operations cannot then be seen even though the optical system looks out on it at along a 160° line of sight, and also because it increases the diameter of the device.

OBJECT OF THE INVENTION

It is an object of the invention firstly to keep the diameter of the forceps instrument and its optical system as small as possible, and secondly to arrange the optical system in such a way that the area between the jaws or in other words the area of operations can be observed directly.

SUMMARY OF THE INVENTION

In accordance with the invention, in the clip forceps previously referred to, the observation system and its viewing tube are made to extend centrally through a barrel which can be moved longitudinally to open and close the jaws of the forceps and so that the observation system is allowed to look out in a straight line from between the jaws of the forceps at the distal end. This gives a shape of smaller cross-section in comparison with known clip forceps, which is important from the patient's point of view, and the area of operations can now be observed directly.

BRIEF DESCRIPTION OF THE DRAWINGS

In order that the invention shall be more clearly understood, reference will now be made to the accompanying drawings which show one embodiment thereof by way of example.

FIG. 1 shows a side-view of the clip forceps instrument according to the invention, FIG. 2 shows an interrupted longitudinal cross-section through the forceps instrument of FIG. 1, FIG. 3 shows an enlarged cross-section along line A–B of FIG. 2, and FIG. 4 shows an enlarged cross-section along line C–D of FIG. 2

SPECIFIC DESCRIPTION OF A PREFERRED EMBODIMENT

Referring now to the drawings, the clip forceps instrument shown consists of a tubular barrel 1, a flooding sleeve 2, a pair of forceps jaws 3, 4, a scissors-grip 5 and an internal viewing tube 6 which is rigidly secured to a cylindrical part 7 at the distal end by soldering or the like. At the proximal end a collar 9 on a taper-turned part 8 projects into the flooding sleeve 2 and between the collar 9 and the viewing tube 6 is mounted a spacer bush 10. Grub-screws 11 and 12 clamp parts 2, 6, 8, 9 and 10 together into a solid unit.

The cylindrical part 7 has, towards the distal end, two longitudinally orientated recesses 13 in which are mounted the limbs 3a and 4a of the two jaws 3 and 4 of the forceps. A locking ring 14 is firmly engaged in suitable square-cornered annular grooves in the cylindrical part 7 and in the limbs 3a, 4a of te two jaws. To allow it to be inserted in the annular grooves this ring is divided and it is secured to the cylindrical part 7 to form a solid whole by means to two small rivets 15.

The limbs 3a, 4a of the jaws 3, 4 allow the jaws to be spring-loaded outwards in the way shown. To provide a seal within the instrument against gas, e.g. carbon dioxide, escaping from the abdominal cavity, sealing rings 16, 17 are fitted into appropriate annular grooves in parts 7 and 10 at the distal and proximal ends.

The scissors grip consists of a usual pair of handles 18 and 19 which are connected together by a pivot screw 20. A leaf spring, which is fixed to handle 18 by a knurled screw and which at the other end has a hinged, that is to say articulated connection to an ear 22 on handle 19, holds the forceps permanently in the open position. Part 18 of the grip of the forceps is securely connected to the flooding sleeve 2 by soldering.

A square cut-out in the free end of handle 19 (FIG. 4) engages via a projection 23a on the U-shaped bolt (pusher) 23 and is securely soldered to this latter. The internal recess in the pusher is such as to leave room for the inner tube 6 and the latter is therefore enclosed. The overflow sleeve is tailored to the external form of the pusher and it is milled away at 24 for a distance appropriate to the movement of the jaws. Because of the configuration of the pusher it is impossible for the axially movable assembly in the forcep instrument (handle 19, pusher 23 and tubular barrel 1) to turn.

There is however no necessity for the scissors grip 5 and the pair of jaws 3, 4 forming the mouth parts to lie in the same plane in the way shown in the drawing. It is even advantageous for the handle to be displaced angularly in relation to the jaws by approximately 30° to 35° since when looking through the optical system the operator holds the grip at the top and can thus manage better if the handle is offset.

The end (not shown) of the optical system 25 (which has an eyepiece 26 and a laterally arranged connection 27 which projects at right angles or is directed obliquely backwards and which allows a light-conducting cable to be connected), is tapered for engagement in the taper in the taper-turned part 8 and is secured to the forceps by means of a union nut 28 and a screw 29. A suitable form of locking is provided so that the light connection 27 will be in the right place, i.e. so that the light-conducting cable leading to the light source will get in the doctor's way as little as possible.

For accurate lining-up the spacer bush 10 therefore has a circumferential V-groove in which fixing screw 11 engages. This adjustment can also be used to move the pair of jaws 3, 4 described above to the appropriate position relative to the handle 5.

The optical system has a 180° line of sight so that it can see straight into the area of operations, that is to say between the jaws 3, 4. It is set slightly back in the cylindrical part 7 at the distal end so as not to be damaged.

The method of operation is as follows: a tantalum clip 31 is fitted between the two open jaws 3, 4. The forcep instrument and with it the optical system are then inserted in the abdominal cavity and the Fallopian tube surrounded under visual observation. The doctor takes hold of handle 19 and moves it towards handle 18 in opposition to spring 21. When this is done the barrel 1 moves in the distal direction in relation to the optical system, slides over the jaws 3, 4 forming the mouth and as it does so closes the pair of jaws and thus the clip 31. The Fallopian tube is sealed off and passage through it blocked. if the doctor now releases his pressure on grip 19, spring 21 will propel it to its original position and at the same time barrel 1 will slide back and the jaws 3, 4 of the forceps wil open again as a result of their spring action.

I claim:
1. A forceps instrument comprising in combination,
  a. an outer sleeve member,
  b. a guiding viewing-tube support, tubular in shape, and mounted concentrically within said outer sleeve,
  c. a tubular barrel mounted within said outer sleeve substantially concentrically around and axially slidable along said guiding viewing-tube support,
  d. optical viewing means including a viewing tube immoveably mounted on and substantially concentrically within said guiding viewing-tube support and extending substantially centrally therethrough such that an uninterrupted line-of-sight is provided therethrough,
  e. a pair of separately pivotally mounted opposing jaws mounted on a distal end of said guiding viewing-tube support and being pivotal apart from and toward one another on opposite sides of said uninterrupted line-of-sight, said jaws being adapted, in an open state, for receiving a tantalum clip therebetween, each of said opposing jaws being further provided with a longitudinally extending jaw limb which is releasably mounted in a correspondingly-shaped, longitudinally extending recess in the outer periphery of said guiding viewing-tube support at its distal end,
  f. locking means for retaining said jaw limbs in said logitudinal recesses, said locking means comprising a locking ring mounted in an annular groove provided in the outer periphery of said guiding viewing-tube support in surrounding relationship to said jaw limbs, and
  g. hand-operated jaw actuation means comprising a first lever element fixedly mounted on a proximal end of said outer sleeve, and a second lever element pivotally mounted on said first lever at an intermediate point thereon, said levers being further interconnected by spring means which biases them into an open position, said second lever being provided at one end with a U-shaped projection which extends through a cut-out in said proximal end of said outer sleeve and said projection is permanently attached to a proximal end of said tubular barrel so that, upon pivotal actuation of said second lever toward said first lever against the bias of said spring means, said tubular barrel is moved along said guiding viewing-tube support in a distal direction to close said jaws and thereby crimp said tantalum clip positioned therebetween, and upon release of said lever, said spring means biases and thereby moves said tubular barrel in a proximal direction along said guiding viewing-tube support and thereby opens said jaws, and the entire crimping operation of the jaws is viewed through said optical means.

* * * * *